United States Patent
Berdami

(10) Patent No.: US 6,274,555 B1
(45) Date of Patent: Aug. 14, 2001

(54) COMPOSITION AND METHOD FOR TOPICAL ANIMAL MEDICATION

(76) Inventor: Lisa A. Berdami, 633 Old Country Club Rd., Meridian, MS (US) 39305

(*) Notice: Subject to any disclaimer, the term of this patent is extended or adjusted under 35 U.S.C. 154(b) by 0 days.

(21) Appl. No.: 09/571,443

(22) Filed: May 15, 2000

(51) Int. Cl.⁷ .......................... A61K 38/00; A61K 31/70; A61K 47/00
(52) U.S. Cl. ................................ 514/15; 514/18; 514/39; 514/783
(58) Field of Search .................. 514/39, 18, 15, 514/783

(56) References Cited

U.S. PATENT DOCUMENTS

| | | |
|---|---|---|
| 3,696,811 * | 10/1972 | Chen ........................................ 602/56 |
| 3,826,232 * | 7/1974 | Duffey et al. ........................ 119/652 |
| 4,209,543 | 6/1980 | Sprecker et al. . |
| 4,284,819 | 8/1981 | Sprecker et al. . |
| 4,289,661 | 9/1981 | Vinals et al. . |
| 4,305,411 | 12/1981 | Sprecker et al. . |
| 4,332,970 | 6/1982 | Sprecker et al. . |
| 4,503,070 | 3/1985 | Eby, III . |
| 4,956,385 | 9/1990 | Eby, III . |
| 5,002,970 | 3/1991 | Eby, III . |
| 5,643,574 | 7/1997 | Gould-Fogerite et al. . |
| 5,840,707 | 11/1998 | Mannino et al. . |
| 5,994,318 | 11/1999 | Gould-Fogerite et al. . |
| 6,070,557 * | 6/2000 | Hibbert ................................ 119/850 |

* cited by examiner

Primary Examiner—William R. A. Jarvis
Assistant Examiner—Vickie Kim
(74) Attorney, Agent, or Firm—John D. Gugliotta

(57) ABSTRACT

A composition for topically treating epidermal abrasions in animals is provided consisting of bacitracin zinc utilized in a ratio of 300 milligrams, neomycin utilized in a ratio of 35 milligrams, polymycin-B sulfate in a ratio of 10,000 milligrams, and pramoxine hydrochiomide in a ration of 10 milligrams. White petroleum jelly is used as a solvent and carrier for the active ingredients. The addition of a bittering agent of bitter apple oil, or citrullus colocynthis, as a powder in a proportion of 2 to 5 grains imparts a bitter flavor to the composition such as to prevent common house pets, such as dogs or cats, from licking their wounds.

4 Claims, No Drawings

COMPOSITION AND METHOD FOR TOPICAL ANIMAL MEDICATION

RELATED APPLICATIONS

The present invention was first described in Disclosure Document No. 468,353, filed on Jan. 31, 2000. There are no previously filed, nor currently any co-pending applications, anywhere in the world.

BACKGROUND OF THE INVENTION

1. Field of the Invention

The present invention relates generally to topical compositions used in the treatment of a skin abrasions and the like in animals and, more particularly, to a topical composition containing a bittering agent for preventing common house pets, such as dogs and cats, from licking their wounds.

2. Description of the Related Art

When an animal or pet has a wound, whether obtained accidentally or as the result of a surgery, it is common instinct of the animal to lick the wound. This licking action not only extends the healing time at the best, it may cause further aggravation or injury at the worst to the animal. Additionally, this licking action is a great source of concern and attention on the part of the pet owner. Also, any creme or ointment placed on the wound is quickly removed thus causing the loss of any healing properties. In the past, large, extended "clown collars" or cones placed around the neck of the animal have been used to limit this licking instinct, but their use is usually less than satisfactory, since the animal usually finds a way around such limitations.

The following patents disclose flavor-masked ionizable zinc compositions for oral absorption.

U.S. Pat. No. 5,002,970 issued in the name of Eby, III
U.S. Pat. No. 4,956,385 issued in the name of Eby, III
U.S. Pat. No. 4,503,070 issued in the name of Eby, III The following patents describe acetyl hydrindacenes, acetyl indanes, and mixtures of same for foodstuff or medicine flavor.

U.S. Pat. No. 4,332,970 issued in the name of Sprecker et al.
U.S. Pat. No. 4,305,411 issued in the name of Sprecker et al.
U.S. Pat. No. 4,289,661 issued in the name of Vinais et al.
U.S. Pat. No. 4,284,819 issued in the name of Sprecker et al.
U.S. Pat. No. 4,209,543 issued in the name of Sprecker et al.

U.S. Pat. No. 5,994,318 issued in the name of Gould-Fogerite et al. discloses cochleate delivery vehicles that include flavored medicines.

U.S. Pat. No. 5,840,707 issued in the name of Mannino et al. describes stabilizing and delivery means of biological molecules.

U.S. Pat. No. 5,643,574 issued in the name of Gould-Fogetite et al. discloses protein- or peptide-cochleate vaccines and methods of immunizing.

Consequently, a need Accordingly, there is a need for a means by which wounds on a pet or animal can heal in a quick and safe manner without the associated risks and dangers of the animal licking the wound.

SUMMARY OF THE INVENTION

It is therefore an object of the present invention to provide an improved composition for treating topical abrasions on animals.

It is yet another object of the present invention to provide an improved composition for treating topical abrasions on animals that prevents the animals from licking their wounds.

It is a feature of the present invention to provide a novel use for a topical preparation containing a bittering agent.

Briefly described according to one embodiment of the present invention, composition and method for topical animal medication is provided as medical ointment for use on animals in the treatment of wounds or healing after surgery. The ointment not only contains an antibiotic to prevent infection but a bitter flavoring that is unpleasant should the animal try to lick it. The bitter flavoring could be caused by the addition of a bitter apple flavoring or other similar tasting substance. The use of the bitter flavoring will cause the pet to cease their licking action after one or two tastes. With the instinct to lick the sore removed, no longer will large collars or cones be required to be worn by the pet or animal. The sore will quickly heal due to the lack of licking and the addition of the antibiotic agent will reduce the chance for infection.

The use of the present invention allows for the speedy healing of wounds on animals caused by accidents or surgery without risk of licking of the sore by the animal.

Advantages of the present invention are that is provides for quick healing time, and reduces risk of infection.

DESCRIPTION OF THE PREFERRED EMBODIMENTS

It has now been discovered that a topical application of antibiotic solution applied directly to an effected area of skin can reduce the risk of primary and secondary infections in both humans and animals. For purposes of disclosing the best mode of the present invention, it is felt that a variety of reactive antibiotics can be used, in combination, to combat infection from a number of sources. Accordingly, active ingredients include bacitracin zinc, neomycin, polymycin-B sulfate, and pramoxine hydrochloride. Although various combinations of these ingredients can be used in various proportions, bacitracin zinc is utilized in a ratio of 300 milligrams, neomycin is utilized in a ration of 35 milligrams, polymycin-B sulfate in a ratio of 10,000 milligrams, and pramoxine hydrochloride in a ratio of 10 milligrams.

Although the art is replete with examples of nonreactive substances that can be utilized to provide this function, and although it is currently envisioned that a variety of these substances may be substituted, it has been found that white petroleum jelly is effective and preferred as a solvent and carrier for the active ingredients.

Finally, the main enablement of the present invention is the addition of a bittering agent to the above composition. In it preferred embodiment, it is felt that the addition of bitter apple oil, or citrullus colocynthis, as a powder in a proportion of 2 to 5 grains.

The foregoing description is included to illustrate the operation of the preferred embodiment and is not meant to limit the scope of the invention. From the forgoing description, many variations will be apparent to those skilled in the art that would yet be encompassed by the spirit and scope of the invention. Therefore, the scope of the invention is to be limited only by the following claims.

I claim:

1. A composition for topically treating epidermal abrasions in animals consisting essentially of a solution of bacitracin zinc, neomycin, polymycin-B sulfate, and pramoxine hydrochloride solvated in a pharmaceutically acceptable diluent, mixed smoothly to a single-phase preparation, and a bittering agent.

2. The composition for topically treating for topically treating epidermal abrasions in animals as described in claim 1, wherein said pharmaceutically acceptable diluent is white petroleum jelly.

3. The composition for topically treating for topically treating epidermal abrasions in animals as described in claim 1, wherein said bittering agent is citrullus colocynthis powder.

4. A composition for topically treating epidermal abrasions in animals of claim 1, wherein bacitracin zinc is utilized in a ratio of 300 milligrams, neomycin is utilized in a ratio of 35 milligrams, polymycin-B sulfate in a ratio of 10,000 milligrams, and pramoxine hydrochloride in a ratio of 10 milligrams.

\* \* \* \* \*